United States Patent [19]

Denzel et al.

[11] 3,971,800
[45] July 27, 1976

[54] DERIVATIVES OF 1H-TRIAZOLO[4,5-c]PYRIDINE-7-CARBOXYLIC ACIDS AND ESTERS

[75] Inventors: Theodor Denzel, Regensburg; Hans Hoehn, Tegernheim, both of Germany

[73] Assignee: E. R. Squibb & Sons, Inc., Princeton, N.J.

[22] Filed: Sept. 10, 1975

[21] Appl. No.: 612,060

Related U.S. Application Data

[62] Division of Ser. No. 471,537, May 20, 1974, Pat. No. 3,929,812.

[52] U.S. Cl. .......................... 260/295.5 B; 424/266
[51] Int. Cl.² ........................................ C07D 213/55
[58] Field of Search ............................ 260/295.5 B

[56] References Cited
UNITED STATES PATENTS 3,763,172 10/1973 Denzel et al. ................ 260/295.5 B
3,862,947 1/1975 Denzel et al. ................ 260/295.5 B

*Primary Examiner*—Alan L. Rotman
*Attorney, Agent, or Firm*—Lawrence S. Levinson; Merle J. Smith

[57] ABSTRACT

New derivatives of 1H-triazolo[4,5-c]pyridine-7-carboxylic acids and esters and their acid addition salts having the general formula

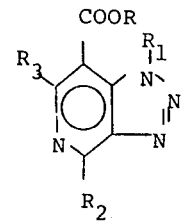

are disclosed. They are useful as anti-inflammatory agents and central nervous system depressants. In addition, this type of compound increases the intracellular concentration of adenosine-3′,5′-cyclic monophosphate.

4 Claims, No Drawings

DERIVATIVES OF 1H-TRIAZOLO[4,5-C]PYRIDINE-7-CARBOXYLIC ACIDS AND ESTERS

This application is a division of application Ser. No. 471,537, filed May 20, 1974, U.S. Pat. No. 3,929,812, Dec. 30, 1975.

SUMMARY OF THE INVENTION

This invention relates to the new derivatives of 1H-triazolo[4,5-c]pyridine-7-carboxylic acids and esters, and acid addition salts thereof, having the general formula (I) 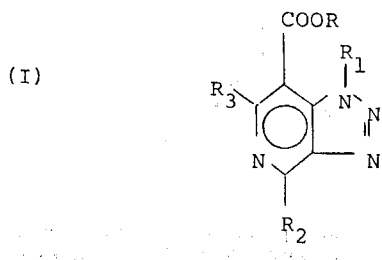

The symbols have the following meaning in formula I and throughout this specification.

R is hydrogen or lower alkyl.

$R_1$ is hydrogen, lower alkyl, phenyl or phenyl-lower alkyl.

$R_2$ is lower alkoxy, or a basic nitrogen group

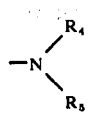

wherein $R_4$ is hydrogen, lower alkyl, di(lower alkyl)amino (lower alkyl) and $R_5$ is hydrogen, lower alkyl or phenyl. The basic group may also form a saturated heterocyclic of 5 or 6 members in which an additional nitrogen is present, i.e., pyrrolidino, piperidino, pyrazolyl, pyrimidino, pyridazinyl or piperazino, each of which may bear as a substituent a hydroxy-lower alkyl group or one or two lower alkyl groups especially the piperidine and piperazine heterocyclics. $R_2$ may also be a hydrazine

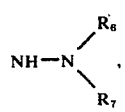

or a hydrazone

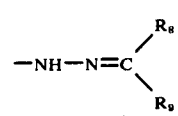

wherein $R_6$, $R_7$ and $R_8$ each is hydrogen, lower alkyl or phenyl, and $R_9$ is lower alkyl or phenyl.

$R_3$ is hydrogen, lower alkyl or phenyl.

The lower alkyl groups referred to throughout this specification include straight or branched chain hydrocarbon groups containing 1 to 7 carbon atoms, preferably 1 to 4 carbons. Examples of the type of groups contemplated are methyl, ethyl, propyl, isopropyl, etc. The lower alkoxy groups include such lower alkyl groups bonded to an oxygen, e.g., methoxy, ethoxy, propoxy, isopropoxy, etc. The phenyl-lower alkyl groups include such lower alkyl groups bonded to a phenyl, e.g., benzyl, phenethyl, etc.

Preferred embodiments of this invention are as follows:

R is hydrogen or lower alkyl of 1 to 4 carbons, especially ethyl.

$R_1$ is hydrogen or lower alkyl of 1 to 4 carbons, especially ethyl or butyl.

$R_2$ is lower alkoxy of 1 to 4 carbons, especially ethoxy, amino, lower alkylamino of 1 to 4 carbons, especially ethylamino or butylamino,

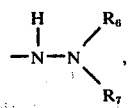

wherein $R_6$ is hydrogen and $R_7$ is hydrogen or lower akyl of 1 to 4 carbons, especially wherein both $R_6$ and $R_7$ are hydrogen, or

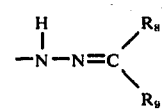

wherein $R_8$ and $R_9$ are both methyl.

$R_3$ is hydrogen or lower alkyl of 1 to 4 carbons, especially methyl.

DETAILED DESCRIPTION OF THE INVENTION

The new compounds of formula I are formed by the following series of reactions.

A 4,6-dihydroxypyridine carboxylic acid ester of the formula (II) 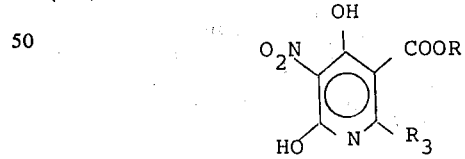

[produced analogous to the procedure described in Chem. Ber. 99, 244, 1966] is made to react with an inorganic acid chloride like phosphorus oxychloride, producing a compound of the formula (III) 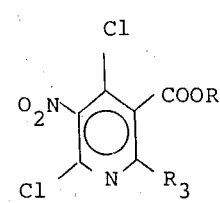

with chlorine atoms in 4- and 6-positions of the molecule. This compound is now treated in an organic solvent like alcohol with the appropriate amine of the formula (IV)

at about 80° C in the presence of a base, e.g., an alkylamine like triethylamine. By this reaction a product of the formula (V)

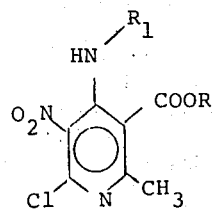

is obtained.

This compound of formula V is made to react with an alkali metal alcoholate. By this procedure a compound of the formula (VI)

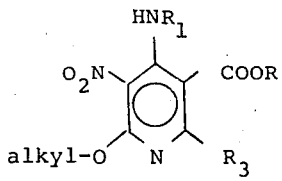

is produced with an alkoxy group in the 6-position of the molecule. This compound is now hydrogenated either catalytically or with a metal-acid pair such as zinc in acetic acid. This results in the formation of a compound of the formula (VII)

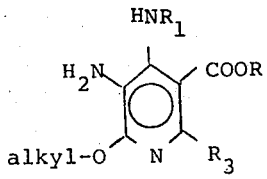

Compounds of the formula (Ia)

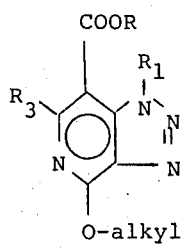

wherein $R_2$ is alkoxy are now produced by reacting a compound of formula VII with an alkali metal nitrite in an acid medium, e.g., sodium nitrite in acetic acid. Compounds of the formula (Ib)

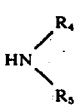

wherein $R_2$ is an amino group are produced by the reaction of a compound of formula Ia with an amine of the formula

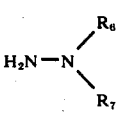 (VIII)

It is sometimes necessary to utilize an autoclave for this reaction. Compounds of the formula (Ic)

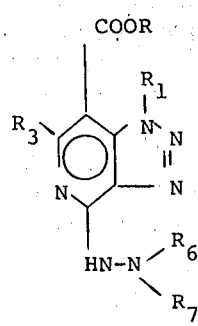

wherein $R_2$ is a hydrazino group are obtained by the reaction of a compound of formula Ia with an appropriate hydrazine of the formula $H_2N-N\overset{R_6}{\underset{R_7}{\diagup}}$ (IX)

Compounds of the formula (Id)

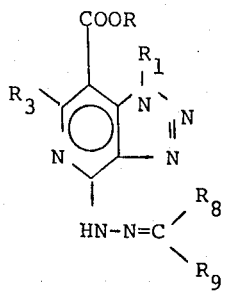

are produced by the reaction of a compound of formula Ic wherein $R_6$ and $R_7$ are both hydrogen, with an appropriate aldehyde or ketone of the formula

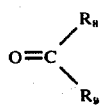  (X)

Compounds of formula Ib, wherein $R_4$ and $R_5$ are not hydrogen are alternatively produced by the reaction of a compound of formula V with the appropriate amine of the formula

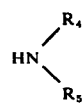  (XI)

producing a compound of the formula (XII)

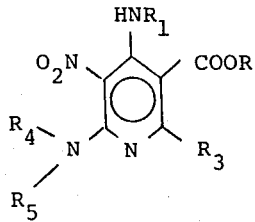

which is now processed as described above, i.e., hydrogenation and subsequent reaction with the alkali metal nitrite in acid medium.

The free acid, wherein R is hydrogen, is obtained by hydrolysis of the ester, e.g., by treatment with an aqueous base like sodium hydroxide solution.

The bases of formula I form pharmaceutically acceptable acid addition salts by reaction with equivalent amounts of the common inorganic and organic acids. Such salts include the hydrohalides, e.g., hydrobromide, hydrochloride, sulfate, nitrate, phosphate, acetate, citrate, oxalate, tartrate, maleate, succinate, benzoate, ascorbate, alkanesulfonate, e.g., methanesulfonate, arylsulfonate, e.g., benzenesulfonate, toluenesulfonate, etc. It is frequently convenient to purify or isolate the product by forming an insoluble salt. The base is obtained by neutralization and another salt then formed by treatment with the appropriate acid.

The new compounds of this invention have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 5 to 40 mg/kg/day, preferably 5 to 20 mg/kg/day, in single or 2 to 4 divided doses, as indicated by the carageenan edema assay in rats. The active substance can be utilized in compositions such as tablets, capsules, solutions or suspensions containing up to about 300 mg. per unit of dosage of a compound or mixture of compounds of formula I or physiologically acceptable acid addition salt thereof. They can be compounded in conventional manner with a physiologically acceptable vehicle or carrier, excipient, binder, preservative, stabilizer, flavor, etc. as called for by accepted pharmaceutical practice. Topical preparations containing about 0.01 to 3 percent by weight of active substance in a lotion, salve or cream may also be used.

The new compounds of this invention are central nervous system depressants and can be used as tranquilizers or ataractic agents for the relief of anxiety and tension states, for example, in mice, cats, rats, dogs and other mammalian species, in the same manner as chlordiazepoxide. For this purpose a compound or mixture of compounds of formula I, or non-toxic, physiologically acceptable acid addition salt thereof is administered orally or parenterally in a conventional dosage form such as tablet, capsule, injectable or the like. A single dose, or preferably 2 to 4 divided daily doses, provided on a basis of about 1 to 3 mg. per kilogram per day, preferably about 2 to 15 mg. per kilogram per day, is appropriate. These may be conventionally formulated in an oral or parenteral dosage form by compounding about 10 to 300 mg. per unit of dosage with conventional vehicle, excipient, binder, preservative, stabilizer, flavor or the like as called for by accepted pharmaceutical practice.

The new compounds also increase the intracellular concentration of adenosine-3',5'-cyclic monophosphate, and thus by the administration of about 1 to 50 mg/kg/day, preferably about 10 to 50 mg/kg, in single or two to four divided doses in conventional oral or parenteral dosage forms such as those described above may be used to alleviate the symptoms of asthma.

The following examples are illustrative of the invention and constitute preferred embodiments. Other members of the class are produced by the procedures illustrated by appropriate substitution of the principal reactants. All temperatures are in degrees celsius.

EXAMPLE 1

4-Ethoxy-1-ethyl-6-methyl-1H-1,2,3-triazolo[4,5-c]pyridine-7-carboxylic acid, ethyl ester a. 4,6-Dichloro-2-methyl-5-nitropyridine-3-carboxylic acid ethyl ester 242 g. of 4,6-dihydroxy-2-methyl-5-nitropyridine-3-carboxylic acid ethyl ester (1 mol.) are heated at 120° with 500 ml. of phosphorus oxychloride for 3 hours. After this time, the excess phosphorus oxychloride is removed in vacuo and the black residue is decomposed by pouring into ice-water. About 1 liter of chloroform is added and the mixture is filtered to remove undissolved material. The organic layer is separated and the aqueous phase is extracted twice with 100 ml. portions of chloroform. The extract is dried over calcium chloride, filtered and evaporated to dryness. The resulting oil is crystallized with about 500 ml. benzene, yielding 153 g. of 4,6-dichloro-2-methyl-5-nitropyridine-3-carboxylic acid ethyl ester (55%); m.p. 45°–46°.

b. 6-Chloro-4-ethylamino-2-methyl-5-nitropyridine-3-carboxylic acid ethyl ester 27.9 g. of 4,6-dichloro-2-methyl-5-nitropyridine-3-carboxylic acid ethyl ester (0.1 mol.) are dissolved in 100 ml. of ethyl alcohol and 12 g. of triethylamine. At reflux temperature a solution of 4.5 g. of ethylamine in 50 ml. of alcohol is slowly added dropwise with continual stirring. After the addition is completed, the reaction mixture is refluxed for an additional 30 minutes. The solvent is then removed in vacuo and the residue is dissolved in 300 ml. of petroleum ether. The triethylamine hydrochloride is filtered off and the filtrate cooled to 0°; 6-chloro-4-ethylamino-2-methyl-5-nitropyridine-3-carboxylic acid ethyl ester crystallizes, yield: 69%, m.p. 36°–37° (methanol).

c. 4-Ethylamino-6-ethoxy-5-nitro-2-methylpyridine-3-carboxylic acid ethyl ester 287 g. of 6-chloro-4-ethylamino-5-nitro-2-methyl-pyridine-3-carboxylic acid ethyl ester (1 mol.) are slowly added to a gently refluxing mixture of 24 g. of sodium in 750 ml. of dry alcohol. The mixture is heated with stirring for an additional hour. After cooling to room temperature, the sodium chloride is filtered off and the filtrate evaporated to dryness. The oily residue of 4-ethylamino-6-ethoxy-5-nitro-2-methylpyridine-3-carboxylic acid ethyl ester is crystallized with methanol, yield 305 g. (82%); m.p. 40°–42°.

d. 5-Amino-4-ethylamino-6-ethoxy-2-methylpyridine-3-carboxylic acid ethyl ester 166 g. of 4-ethylamino-6-ethoxy-5-nitro-2-methylpyridine-3-carboxylic acid ethyl ester are dissolved in 500 ml. of butyl alcohol. 300 mg. of palladium on charcoal (10%) are added and the mixture is hydrogenated at 80°. After the theoretical amount of hydrogen has been absorbed, the solution is filtered and the solvent distilled off. Distillation of the remaining colorless oil yields 125 g. of 5-amino-4-ethylamino-6-ethoxy-2-methylpyridine-3-carboxylic acid ethyl ester, b.p. 170–175/$_{0.05}$.

e. 4-Ethoxy-1-ethyl-6-methyl-1H-1,2,3-triazolo[4,5-c]pyridine-7-carboxylic acid ethyl ester 26.7 g. of 5-amino-4-ethylamino-6-ethoxy-2-methyl-pyridine-3-carboxylic acid ethyl ester (0.1 mol.) are dissolved in 100 ml. of acetic acid. At room temperature 7.5 g. of sodium nitrite in 20 ml. of water are added dropwise with continual stirring. The temperature is kept below 20°. The mixture is stirred overnight and then evaporated to dryness. 100 ml. of water are added to the residue which is then extracted three times with 50 ml. portions of ether. The organic layer is collected, dried over sodium sulfate, filtered and the solvent distilled off. The residue of 4-ethoxy-1-ethyl-6-methyl-1H-1,2,3-triazolo[4,5-c]pyridine-7-carboxylic acid ethyl ester is recrystallized from ligroin, yield 75%, m.p. 56°–58°.

f. 4-Ethoxy-1-ethyl-6-methyl-1H-1,2,3-triazolo[4,5-c]pyridine-7-carboxylic acid 20 g. of 4-ethoxy-1-ethyl-6-methyl-1H-1,2,3-triazolo[4,5-c]pyridine-7-carboxylic acid ethyl ester are hydrolyzed with aqueous sodium hydroxide to obtain 4-ethoxy-1-ethyl-6-methyl-1H-1,2,3-triazolo[4,5-c]pyridine-7-carboxylic acid.

The following additional compounds are obtained by the foregoing procedure:
1-Ethyl-4-methoxy-6-methyl-1H-1,2,3-triazolo[4,5-c]-pyridine-7-carboxylic acid methyl ester.
4-n-butoxy-1-methyl-1H-1,2,3-triazolo[4,5-c]pyridine-7-carboxylic acid n-butyl ester.
1,6-diethyl-4-ethoxy-1H-1,2,3-triazolo[4,5-c]pyridine-7-carboxylic acid and ethyl ester.
4-Pentoxy-1H-1,2,3-triazolo[4,5-c]pyridine-7-carboxylic acid and ethyl ester.
4-Ethoxy-1-ethyl-6-phenyl-1H-1,2,3-triazolo[4,5-c]-pyridine-7-carboxylic acid ethyl ester.
4-Methoxy-1-phenyl-1H-1,2,3-triazolo[4,5-c]pyridine-7-carboxylic acid methyl ester.
4-Propoxy-6-methyl-1H-1,2,3-triazolo[4,5-c]pyridine-7-carboxylic acid propyl ester.
4-Ethoxy-1-ethyl-6-propyl-1H-1,2,3-triazolo[4,5-c]-pyridine-7-carboxylic acid ethyl ester.
1-Benzyl-4-methoxy-1H-1,2,3-triazolo[4,5-c]pyridine-7-carboxylic acid methyl ester.
4-Ethoxy-6-methyl-1-phenethyl-1H-1,2,3-triazolo-[4,5-c]pyridine-7-carboxylic acid ethyl ester.
4-Ethoxy-6-methyl-1-phenyl-1H-1,2,3-triazolo[4,5-c]-pyridine-7-carboxylic acid and methyl ester.
4-Ethoxy-1H-1,2,3-triazolo[4,5-c]pyridine-7-carboxylic acid ethyl ester.
4-Ethoxy-1-phenethyl-1H-1,2,3-triazolo[4,5-c]pyridine-7-carboxylic acid ethyl ester.

EXAMPLE 2

4-Butylamino-1-ethyl-6-methyl-1H-1,2,3-triazolo[4,5-c]pyridine-7-carboxylic acid ethyl ester 2.8 g. of 4-ethoxy-1-ethyl-6-methyl-1H-1,2,3-triazolo[4,5-c]pyridine-7-carboxylic acid ethyl ester is treated for 14 hours with 10 ml. of n-butylamine at reflux temperature. The excess butylamine is distilled off and the residue of 4-butylamino-1-ethyl-6-methyl-1H-1,2,3-triazolo[4,5-c]pyridine-7-carboxylic acid ethyl ester is recrystallized from petroleum ether, yield 78%, m.p. 85°–87°.

EXAMPLE 3

1-Ethyl-6-methyl-4-isopropylamino-1H-1,2,3-triazolo[4,5-c]-pyridine-7-carboxylic acid ethyl ester By substituting isopropylamine for the n-butylamine in the procedure of Example 2, 1-ethyl-6-methyl-4-isopropyl-1H-1,2,3-triazolo[4,5-c]pyridine-7-carboxylic acid ethyl ester is obtained, yield 83%, m.p. 55°–57° (petroleum ether).

The following additional compounds are obtained by the procedure of Example 2 by substituting the appropriate amine for the butylamine and another product of Example 1 for the 4-ethoxy-1-ethyl-6-methyl-1H-1,2,3-triazolo[4,5-c]pyridine-7-carboxylic acid ethyl ester:
1-Ethyl-4-ethylamino-6-methyl-1H-1,2,3-triazolo-[4,5-c]pyridine-7-carboxylic acid methyl ester.
4-Dimethylamino-1-ethyl-6-methyl-1H-1,2,3-triazolo-[4,5-c]pyridine-7-carboxylic acid and ethyl ester.
4-Diethylamino-1-methyl-1H-1,2,3-triazolo[4,5-c]-pyridine-7-carboxylic acid propyl ester.
1,6-diethyl-4-(methylethylamino)-1H-1,2,3-triazolo-[4,5-c]pyridine-7-carboxylic acid ethyl ester.
1-Methyl-4-phenylamino-1H-1,2,3-triazolo[4,5-c]-pyridine-7-carboxylic acid ethyl ester.
4-Amino-6-methyl-1-phenyl-1H-1,2,3-triazolo[4,5-c]-pyridine-7-carboxylic acid and ethyl ester.

4-Amino-6-methyl-1H-1,2,3-triazolo[4,5-c]pyridine-7-carboxylic acid and ethyl ester.
1-Benzyl-4-amino-1H-1,2,3-triazolo[4,5-c]pyridine-7-carboxylic acid methyl ester.
4-n-Butylamino-6-methyl-1-phenethyl-1H-1,2,3-triazolo[4,5-c]pyridine-7-carboxylic acid ethyl ester.

EXAMPLE 4

1-Ethyl-6-methyl-4-[3-(dimethylamino)propyl]amino-1H-1,2,3-triazolo[4,5c]pyridine-7-carboxylic acid ethyl ester (3-Dimethylamino)propylamine is substituted for the n-butylamine in the procedure of Example 2 to obtain 1-ethyl-6-methyl-4-[3-(dimethylamino)propyl]amino-1H-1,2,3-triazolo[4,5-c]pyridine-7-carboxylic acid ethyl ester, yield 79%, m.p. 30°–34° (ethyl acetate).

The following additional products are obtained by the procedure of Example 2 1 by substituting a (lower alkylamino)lower alkylamine for the n-butylamine and another product of Example 1 for the triazolopyridine-carboxylic acid ester:

4-[(2-Diethylamino)ethylamino]-1H-1,2,3-triazolo-[4,5-c]pyridine-7-carboxylic acid ethyl ester.
4-(Dipropylaminomethylamino)-6-methyl-1-phenyl-1H-1,2,3-triazolo[4,5-c]pyridine-7-carboxylic acid and ethyl ester.

EXAMPLE 5

1-Ethyl-4-hydrazino-6-methyl-1H-1,2,3-triazolo-[4,5-c]pyridine-7-carboxylic acid ethyl ester By substituting hydrazine for the amine in the procedure of Example 2, 1-ethyl-4-hydrazino-6-methyl-1H-1,2,3-triazolo[4,5-c]pyridine-7-carboxylic acid ethyl ester is formed, yield 58%, m.p. 75°–78° (ethyl acetate).

The following additional products are obtained by the procedure of Example 2 by substituting hydrazine, alkylhydrazine or phenylhydrazine for the amine and another product of Example 1 for the triazolopyridine ester:

4-(Methylhydrazino)-1-methyl-1H-1,2,3-triazolo[4,5-c]-pyridine-7-carboxylic acid n-butyl ester.
4-(Phenylhydrazino)-1-ethyl-6-methyl-1H-1,2,3-triazolo[4,5-c]pyridine-7-carboxylic acid ethyl ester.
4-(Diethylhydrazino)-1,6-diethyl-1H-1,2,3-triazolo-[4,5-c]pyridine-7-carboxylic acid and ethyl ester.
4-Hydrazino-1H-1,2,3-triazolo[4,5-c]pyridine-7-carboxylic acid ethyl ester.
4-(n-Propylhydrazino)-1H-1,2,3-triazolo[4,5-c]pyridine-7-carboxylic acid ethyl ester.
4-(Dimethylhydrazino)-1-ethyl-6-phenyl-1H-1,2,3-triazolo[4,5-c]pyridine-7-carboxylic acid ethyl ester.
4-(Phenylhydrazino)-1-phenyl-1H-1,2,3-triazolo[4,5-c]-pyridine-7-carboxylic acid methyl ester.
4-(Methylhydrazino)-6-methyl-1H-1,2,3-triazolo-[4,5-c]pyridine-7-carboxylic acid propyl ester.
4-Hydrazino-1-ethyl-6-propyl-1H-1,2,3-triazolo-[4,5-c]pyridine-7-carboxylic acid and ethyl ester.
1-Benzyl-4-methylhydrazino-1H-1,2,3-triazolo[4,5-c]-pyridine-7-carboxylic acid methyl ester.
4-Hydrazino-6-methyl-1-phenethyl-1H-1,2,3-triazolo-[4,5-c]pyridine-7-carboxylic acid ethyl ester.
4-Hydrazino-6-methyl-1-phenyl-1H -1,2,3-triazolo[4,5-c]-pyridine-7-carboxylic acid methyl ester.
1-Benzyl-4-hydrazino-1H-1,2,3-triazolo[4,5-c]pyridine-7-carboxylic acid methyl ester.
4-Hydrazino-6-methyl-1H-1,2,3-triazolo[4,5-c]-pyridine-7-carboxylic acid propyl ester.

EXAMPLE 6

1-Ethyl-6-methyl-4-[2-(1-methylethylidene)hydrazino]-1H-1,2,3-triazolo[4,5-c]pyridine-7-carboxylic acid ethyl ester 2.6 g. of 1-ethyl-4-hydrazino-6-methyl-1H-1,2,3-triazolo[4,5-c]pyridine-7-carboxylic acid ethyl ester (0.01 mol.) are dissolved in 10 ml. of acetone. One drop of acetic acid is added and the mixture is allowed to stand overnight. The excess acetone is distilled off in vacuo and the residue is recrystallized from petroleum ether to obtain 1-ethyl-6-methyl-4-[2-(1-methylethylidene)hydrazino]-1H-1,2,3-triazolo[4,5-c]pyridine-7-carboxylic acid ethyl ester in 95% yield, m.p. 68°–72°.

The following additional compounds are obtained by the procedure of Example 6 by substituting another ketone for the acetone utilizing the same or another hydrazine of Example 6.

1-Ethyl-6-methyl-4-[2-(1-ethylpropylidene)hydrazino]-1H-1,2,3-triazolo[4,5-c]pyridine-7-carboxylic acid ethyl ester.
1-Ethyl-6-methyl-4-[2-(1-methylpropylidene)]hydrazino]-1H-1,2,3-triazolo[4,5-c]pyridine-7-carboxylic acid ethyl ester.
1-Ethyl-6-methyl-4-[2-α-methylbenzylidene)]hydrazino]-1H-1,2,3-triazolo[4,5-c]pyridine-7-carboxylic acid ethyl ester.
4-[2-(1-methylethylidene)hydrazino]-1H-1,2,3-triazolo[4,5-c]pyridine-7-carboxylic acid ethyl ester.
4-[2-(1-methylethylidene)hydrazino]-1-ethyl-6-propyl-1H-1,2,3-triazolo[4,5-c]pyridine-7-carboxylic acid ethyl ester.
4-[2-(1-methylethylidene)hydrazino]-6-methyl-1-phenethyl-1H-1,2,3-triazolo[4,5-c]pyridine-7-carboxylic acid ethyl ester.
4-[2-(1-methylethylidene)hydrazino]-6-methyl-1-phenyl-1H-1,2,3-triazolo[4,5-c]pyridine-7-carboxylic acid methyl ester.
1-Benzyl-4-[2-(1-methylpropylidene)hydrazino]-1H-1,2,3-triazolo[4,5-c]pyridine-7-carboxylic acid methyl ester.
4-[2-(α-methylbenzylidene)hydrazino]-1H-1,2,3-triazolo[4,5-c]pyridine-7-carboxylic acid ethyl ester.
4-[2-(1-methylethylidene)hydrazino]-6-methyl-1H-1,2,3-triazolo[4,5-c]pyridine-7-carboxylic acid propyl ester.

EXAMPLE 7

1-Ethyl-6-methyl-4-[(N-methyl)piperazino]-1H-1,2,3-triazolo-[4,5-c]pyridine-7-carboxylic acid ethyl ester a. 4-Chloro-2-methyl-5-nitro-6-[(N-methyl)-piperazino]pyridine-3-carboxylic acid ethyl ester By substituting (N-methyl)piperazine for the ethylamine in the procedure of Example 1b, 4-chloro-2-methyl-5-nitro-6-[(N-methyl)piperazino)pyridine-3-carboxylic acid ethyl ester is formed, yield 64%, m.p. 62°–64° (methanol).

b. 4-Ethylamino-2-methyl-5-nitro-6-[(N-methyl)-piperazino]-pyridine-3-carboxylic acid ethyl ester 32.7 g. of 4-chloro-2-methyl-5-nitro-6-[(N-methyl)-piperazino]pyridine-3-carboxylic acid ethyl ester (0.1 mol.) and 12 g. of triethylamine are treated with stirring in 100 ml. of alcohol at reflux temperature with 6 g. of ethylamie for 1 hour. After this time, the solution is evaporated and dissolved in 100 ml. of ether. The precipitated triethylamine hydrochloride is filtered off and the filtrate cooled to −30°. 4-Ethylamino-2-methyl-5-nitro-6-[(N-methyl)piperazino]-pyridine-3-carboxylic acid ethyl ester precipitates, yield 73%, m.p. 59°–61° (methanol).

c. 5-Amino- 4-ethylamino-2-methyl-6-[(N-methyl)-piperazino]-pyridine-3-carboxylic acid ethyl ester By substituting 4-ethylamino-2-methyl-5-nitro-6-[(N-methyl)piperazino]pyridine-3-carboxylic acid ethyl ester in the procedure of Example 1d, 5-amino-4-ethylamino-2-methyl-6-[(N-methyl)piperazino]pyridine-3-carboxylic acid ethyl ester is formed, yield 94%, b.p. 210°–220°/$_{0.01}$.

d. 1-Ethyl-6-methyl-4-[(N-methyl)piperazino]pyridine-1H-1,2,3-triazolo[4,5-c]pyridine-7-carboxylic acid ethyl ester By substituting 5-amino-4-ethylamino-2-methyl-6-[(N-methyl)piperazino]pyridine-3-carboxylic acid ethyl ester in the procedure of Example 1e, 1-ethyl-6-methyl-4-[(N-methyl)-piperazino]-1H-1,2,3-triazolo[4,5-c]pyridine-7-carboxylic acid ethyl ester is produced, yield 83%, m.p. 63°–65° (petroleum ether).

EXAMPLE 8

1-Ethyl-6-methyl-4-piperidino-1H-1,2,3-triazolo[4,5-c]pyridine-7-carboxylic acid ethyl ester By substituting piperidine for (N-methyl)piperazine in Example 7a, and this compound processed according to the procedures of Example 7b, c and d, 1-ethyl-6-methyl-4-piperidino-1H-1,2,3-triazolo[4,5-c]pyridine-7-carboxylic acid ethyl ester is formed, m.p. 45°–47° (petroleum ether).

The following additional products are obtained when piperazine, pyrrolidine, piperidine, pyrazoline, pyrimidine, pyridazine or 4-(hydroxyethyl)piperazine is substituted for the ethylamine in the procedure of Example 1b:

1-Ethyl-6-methyl-4-piperizino-1H-1,2,3-triazolo[4,5-c]pyridine-7-carboxylic acid ethyl ester.
1-Ethyl-6-methyl-4-pyrrolidino-1H-1,2,3-triazolo[4,5-c]pyridine-7-carboxylic acid ethyl ester.
1-Ethyl-6-methyl-4-piperidino-1H-1,2,3-triazolo[4,5-c]pyridine-7-carboxylic acid ethyl ester.
1-Ethyl-6-methyl-4-(4-ethylpiperidino)-1H-1,2,3-triazolo[4,5-c]pyridine-7-carboxylic acid ethyl ester.
1-Ethyl-6-methyl-4-pyrazolino-1H-1,2,3-triazolo[4,5-c]pyridine-7-carboxylic acid ethyl ester.
1-Ethyl-6-methyl-4-pyrimidino-1-H-1,2,3-triazolo[4,5-c]pyridine-7-carboxylic acid ethyl ester.
1-Ethyl-6-methyl-4-pyridazino-1H-1,2,3-triazolo[4,5-c]pyridine-7-carboxylic acid ethyl ester.
1-Ethyl-6-methyl-4-[4-(2-hydroxyethyl)piperazino]-1H-1,2,3-triazolo[4,5-c]pyridine-7-carboxylic acid and ethyl ester.

What is claimed is:

1. A compound of the formula

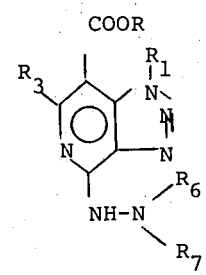

wherein R is hydrogen or lower alkyl; $R_1$ is hydrogen, lower alkyl, phenyl, benzyl or phenethyl; and $R_3$, $R_6$ and $R_7$ each is hydrogen, lower alkyl or phenyl.

2. A compound as in claim 1 wherein R, $R_1$, $R_3$, $R_6$ and $R_7$ each is hydrogen or lower alkyl.

3. A compound as in claim 1 wherein R, $R_1$ and $R_3$ each is lower alkyl and $R_6$ and and $R_7$ each is hydrogen or lower alkyl.

4. A compound as in claim 3 wherein R and $R_1$ each is ethyl; $R_3$ is methyl; and $R_6$ and $R_7$ each is hydrogen.

* * * * *